United States Patent [19]

Schmid et al.

[11] Patent Number: 5,306,149
[45] Date of Patent: Apr. 26, 1994

[54] IMPLANT FOR ATTACHING A SUBSTITUTE TOOTH OR THE LIKE TO A JAW

[75] Inventors: Jürg Schmid, Ilanz; Christoph Hämmerle, Forst; Niklaus P. Lang, Neuenegg; Francis J. Sutter, Hölstein, all of Switzerland

[73] Assignee: Institut Straumann AG, Waldenburg, Switzerland

[21] Appl. No.: 909,559

[22] Filed: Jul. 6, 1992

[30] Foreign Application Priority Data

Jul. 15, 1991 [CH] Switzerland ............... 2099/91

[51] Int. Cl.⁵ ............................................. A61C 8/00
[52] U.S. Cl. ................................................... 433/173
[58] Field of Search ................ 433/173, 174, 175, 176

[56] References Cited

U.S. PATENT DOCUMENTS

| | | | |
|---|---|---|---|
| 3,579,829 | 5/1971 | Samson | 433/173 |
| 3,979,828 | 9/1976 | Taylor | 433/175 |
| 4,702,697 | 2/1986 | Linkow | |
| 4,768,956 | 9/1988 | Kurpis | 433/176 |
| 5,006,070 | 4/1991 | Komatsu | 433/173 |
| 5,052,930 | 10/1991 | Lodde | 433/173 |

FOREIGN PATENT DOCUMENTS 9007308  7/1990  PCT Int'l Appl. .
9114404 10/1991  PCT Int'l Appl. .

Primary Examiner—Gene Mancene
Assistant Examiner—Nicholas D. Lucchesi
Attorney, Agent, or Firm—Akoo-Toren

[57] ABSTRACT

A implant is disclosed particularly for jawbone, comprising a diaphragm and a carrier having an elongated column-like central portion and a frame supporting the central portion, as well as spikes for anchoring the carrier into the jawbone. An intermediate piece for fastening the diaphragm at the end of the central portion are also disclosed. The implant facilitates favorable conditions for growth of the bone tissue so that bone material grows into a space covered by the diaphragm due to the solid anchoring of the implant into the jawbone.

6 Claims, 2 Drawing Sheets

IMPLANT FOR ATTACHING A SUBSTITUTE TOOTH OR THE LIKE TO A JAW

FIELD OF THE INVENTION

The present invention is directed generally to implants and more particularly to an implant for attaching a denture or substitute tooth to a jaw.

BACKGROUND OF THE INVENTION

WO-A-90 07 308 discloses a jaw implant comprising a carrier and a biocompatible diaphragm covering the carrier. The carrier has a central portion with a threaded bore for the attachment of an artificial substitute tooth. The diaphragm is connected to the carrier during insertion of the carrier into a hole in a jawbone so that it covers the area of the jawbone surrounding the carrier and protects it against the growing in of the gingival bindweb and the epithelium tissue, as well as against the penetration of microorganisms. The amount of jawbone available for insertion of such implants however can be so small that an adequate anchoring of the previously described implant is no longer possible. This problem frequently occurs with implants into the upper jaw.

In addition to such implants, implants for attaching substitute tooth are generally known comprising hollow cylindrical sockets provided with apertures and a single piece head portion widening away from the socket. When a substitute tooth is to be fastened with the head portion at a jawbone, the implant is inserted into a hole of the jawbone so that it is approximately flush or above the surface of the jawbone. The bore in the end side of the head portion is then closed off with a sealing screw. The implant now remains in this sealed state in the jawbone during the healing phase, which may, for instance, last for several months. The bone tissue grows during this healing phase into the cylindrical socket which is tightly anchored in the jawbone. The sealing or closing screw is subsequently removed and a secondary element is threaded into the implant. The secondary element forms a post or pillar at which the artificial substitute tooth or denture is fastened.

During the healing phase, the epithelium tissue and the gingival bindweb or connective tissue normally grows faster than the bone tissue of the alveolar extension and especially faster than the cement and the bone cells forming the desmodontal bindweb. After insertion of an implant, the epithelium tissue and the gingival bindweb grow into the gap between the jawbone and the implant and deposit themselves at the implant, whereby the growing-together of the bone tissue and the implant is delayed or even entirely prevented. Such methods however permit microorganisms to penetrate from the mouth cavity into the existing gaps and cause infections.

The problems with such previously known devices were hitherto solved in two different ways. According to one way, bone shavings obtained by a surgical intervention into the pelvic region or portions of ribs of the patient were used for thickening the jawbone. After the jawbone is thickened, one of the known implants is inserted into the intended area of the jawbone. Experiments have shown however that such intervention is very complicated, not always successful and assumes that the transplanted bone tissue grows completely together with the jawbone and the implant. The other type of treatment involves the insertion of an implant into the jawbone, increase and thickening of the bone tissue of the alveolar extension and the cement. In this type of treatment, the bone cells forming the desmodontal bindweb are promoted in a targeted manner. Cells forming this tissue can multiply at the jawbone, if it is isolated from the gingival bindweb during the bone regeneration phase. The isolation can be achieved by using a biocompatible diaphragm between the gingival bindweb and the bone tissue. Such a diaphragm would have pores permitting the passage of gases through the diaphragm and/or the deposition of cells and the growing of such cells into the diaphragm. After bone formation, one of the already known implants could be inserted into the jawbone. Such treatment however has the distinct disadvantage of having at least three chronologically separate operations which makes the entire treatment period approximately twice as long as with a normal implant. The danger of a failure is correspondingly increased.

It is therefore an object of the present invention to provide an implant that has a relatively short treatment period.

Another object of the invention is to provide an implant which permits adequate anchoring to a jawbone or the like.

Still another object of the present invention is to provide a safe implant which additionally prevents the entry of microorganisms from the mouth cavity and into the existing gaps.

Additionally, an object of the invention is to provide an implant which is particularly helpful if the jawbone area to be treated is insufficient for fixing previously known implants.

Yet another object of the invention is to provide an implant which can be replaced upon the jawbone area to be treated without prior bone formation treatment.

SUMMARY OF THE INVENTION

These and other objects of the invention which shall be hereafter apparent are achieved by an implant provided with a threaded bore for fastening a substitute tooth or dentures at the jaw. The implant comprises a carrier and a diaphragm enabling bone formation and intended to cover the carrier. The carrier has a central portion containing the threaded bore and a frame surrounding the central portion. The frame comprises a base formed by transverse ribs and longitudinal ribs and at least four cross ties extending from the base edge. The carrier has at least two spikes for fastening the implant into the jawbone.

The diaphragm enables the consolidation of the implant with the bone tissues and can consist, for instance, of a porous polytetrafluoroethylene known under the trade name GORE-TEX or some other equivalent material. The deposition of microorganisms in the region covered by the diaphragm, as well as the propagation of infection, can be inhibited by such a diaphragm. The invention provides favorable conditions for the growth of new bone tissue in an intermediate space covered by the diaphragm, wherein the deposition of bone material at the implant and its solid anchoring thereon is promoted as well as accelerated.

BRIEF DESCRIPTION OF THE DRAWINGS

The invention will be better understood by the Detailed Description of the Preferred Embodiment, in connection with the drawings, of which.

DETAILED DESCRIPTION OF THE PREFERRED EMBODIMENT

Figure 1:
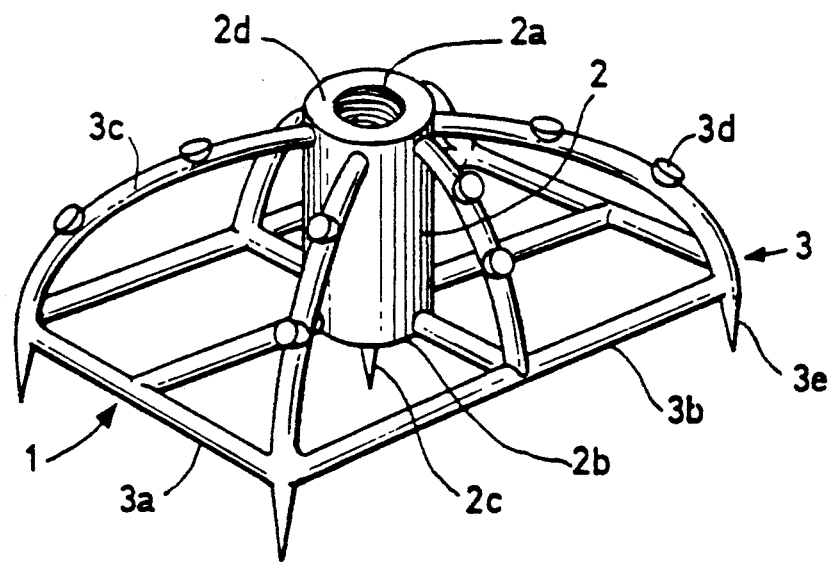
FIG. 1 a perspective view of a single piece carrier or support of an implant.

Referring now to the drawing, wherein like numerals reflect like elements throughout the several views, FIG. 1 is a perspective view of a jaw 1 implant comprising an elongated column-like central portion 2 and a frame 3 surrounding the central portion 2. The central portion 2 can attach a non-depicted artificial tooth or denture and has a threaded bore 2a and a spike 2c for fixing the implant into the jawbone at the closed end 2b at the bottom of the central portion 2. The frame 3 surrounding the central portion 2 comprises a base formed by lateral ribs 3a, longitudinal ribs 3b and six cross-ties 3c extending from the base edge and connected to the upper end of the central portion 2. Each cross-tie 3c has at least two cams or lugs 3d on the side facing away from the base. The base comprises six spikes 3e for fastening the implant onto the jawbone at the crossing points of the transverse ribs 3a and longitudinal ribs 3b.

Figure 2:
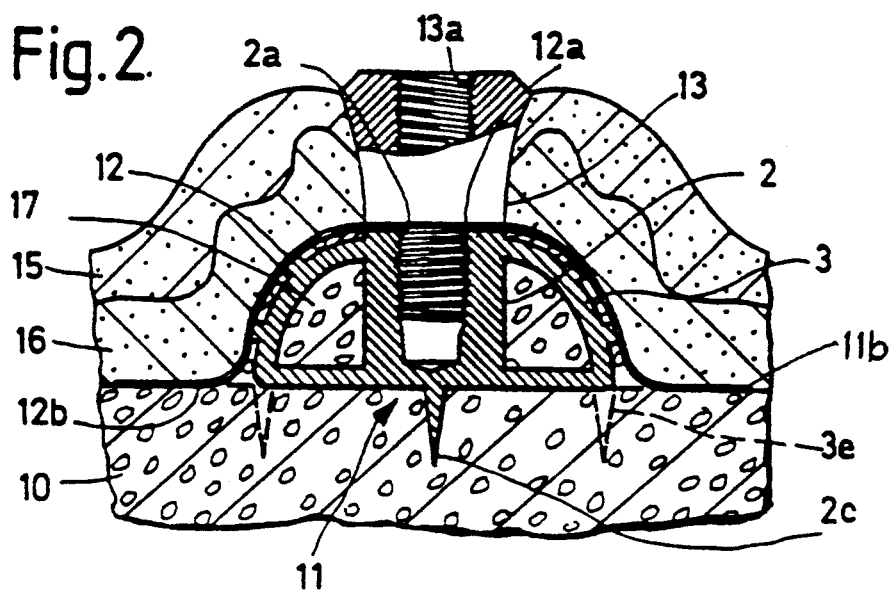
FIG. 2 is a cross-sectional view through a jawbone and an implant with an intermediate piece shown partially in section and partially in front view.

A jawbone 10 and an implant 11 placed thereon in a trans-gingival manner can be seen in FIG. 2. The implant 11 has a diaphragm 12 covering the frame 3 of the carrier and is a flexible foil and has a circularly-shaped aperture 12a at its center corresponding to the bore. The diaphragm 12 is fastened to the central portion 2, covers the frame 3 and rests with its outer edge segment 12b on the surface of the jawbone 20. The diaphragm 12 is held, at least in part, at a spacing from the cross ties 3c by the cams or lugs 3c or the. The ribs 3b are depicted in FIG. 2 as resting on the jawbone.

An intermediate piece 13 is threaded into the upper end 2d of the central portion 2 so that the diaphragm 12 is clamped between this intermediate piece 13 and the central portion 2 in a fluid-tight manner. The intermediate piece 13 has an axially threaded bore 13a and a segment which widens upwards away from the middle portion 2 in an approximately cone-shaped manner that is curved slightly concavely in axial section. The intermediate piece 13 is preferably composed of the same material as the carrier and is a biocompatible material such as stainless steel, titanium or a titanium alloy or reinforced plastics material.

For insertion of the implant, the dental surgeon cuts open the epithelium tissue 15 and the gingival connecting tissue 16 at the point intended for insertion of the implant 11 and exposes the jawbone 10 by rolling away these soft layers of tissue 15 and 16. The carrier of the implant 11, comprising central portion 2 and frame 3, is placed upon the exposed spot of the jawbone 10. Small holes may be made for the spikes 2c and 3e, depending upon the hardness of the bone and to precisely position the carrier. This may be accomplished with a suitable template. Subsequently, the implant 11 comprising the carrier, the diaphragm 12 and the intermediate piece 13 is placed upon the area of the jawbone to be treated. Attention and care must be taken so that the spikes 2c and 3e penetrate into the prepared holes, if they are created. The inserted implant 11 is thereupon covered over, with exception of the intermediate piece 13, by folding the gingival bindwebs 16 and the epithelium tissue 15 back into their proper place.

The diaphragm 12 covers the free space 17 between the cross-ties 3c of the frame 3 and the jawbone 10 against the epithelium tissue 15 and against the gingival binding tissue or bindweb 16. The diaphragm 12 is flexible to such an extent that its outer edge segment 12b can sprightly adapt to the surface region of the jawbone 10 surrounding the base of the implant 11. When the soft tissue layers 15 and 16 cover the diaphragm 12, they also contribute to retain the outer edge segment 12b of the diaphragm 13 at the jawbone 10. The outer edge segment 12b can additionally be secured by holes and biocompatible screws threaded directly into the jawbone 10 and penetrating through the outer edge segment 12b to permit an infiltration beneath the gingival connecting tissue, especially with larger contour dimensions of the diaphragm 12.

After the previously described treatment, the implant 11 is left, during a time period serving as a healing phase in the state shown in FIG. 2. During this healing phase, the bone forming cells proliferate and form new bone tissue which grows into the intermediate space covered by the diaphragm 12. As explained, the formation of the bone tissue is promoted and accelerated by the diaphragm 12.

A secondary element, which is not shown here, is fastened upon the intermediate piece 13 after the healing phase. This element comprises a threaded portion which can be screwed into the threaded bore 13a of the intermediate piece 13 and a post or pillar extruding from the jawbone for carrying or support of a substitute tooth or denture which is not shown here. The secondary element can also directly receive a substitute tooth instead of the pillar or post. Naturally, there is also the possibility of removing the diaphragm 12 even prior to the insertion of the secondary element. For this, one must however cut open the soft tissue layers 15 and 16 which, in the meantime, have healed.

Figure 3:
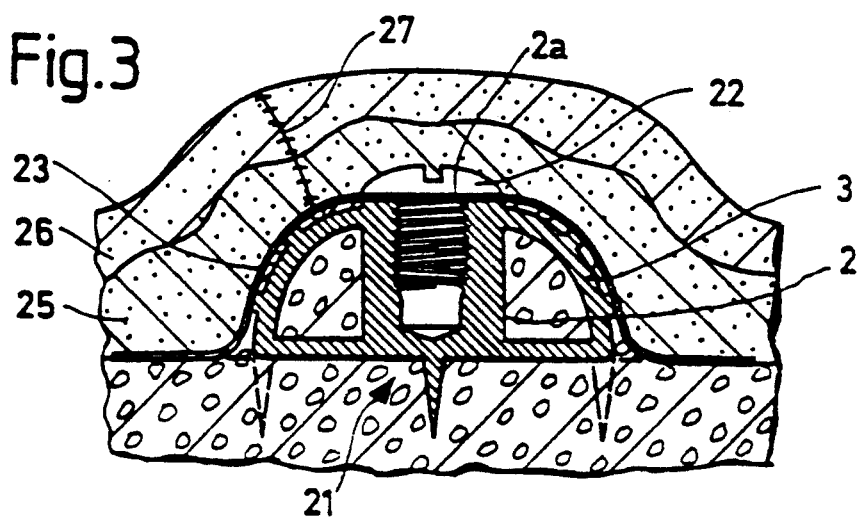
FIG. 3 is a cross-sectional view through a jawbone and an implant with a screw shown partly in section and partially in front view.

The implant designated as 21 and shown in FIG. 3 comprises the same carrier as the implant 11 described in FIG. 2. In treating a patient, the using of implant 21 is, for all intents and purposes, identical with the already described treatment, wherein the threaded bore 28 in the central portion 2 is closed off by a screw 22 which retains the diaphragm 23 at the central portion or part 2. After insertion of the implant 22, it is covered by the gingival bindweb 25 and the epithelium tissue 26 and the area of operation is closed by suture 27.

After the healing phase of the implant 21 shown in FIG. 3, one cuts open the tissues 25 and 26 which, in the meantime, have healed. Thereupon the screw 22 and, if required, the diaphragm 23, are removed and a secondary element, not shown here, is fastened upon the central portion 2. The secondary element is either a substitute tooth or a post protruding from the jawbone for support or carriage of a substitute tooth.

Figure 4:
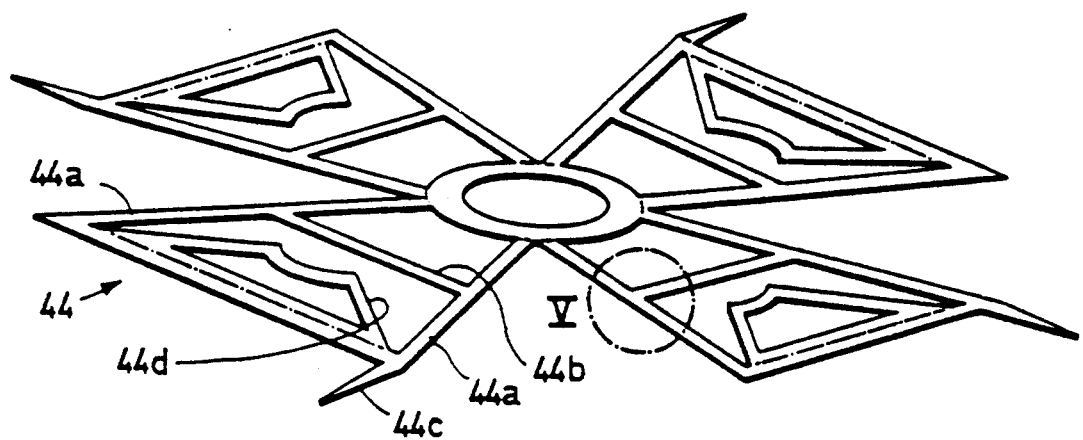
FIG. 4 is a front view of a workpiece used for the manufacture of the frame of a two-part carrier.
Figure 5:
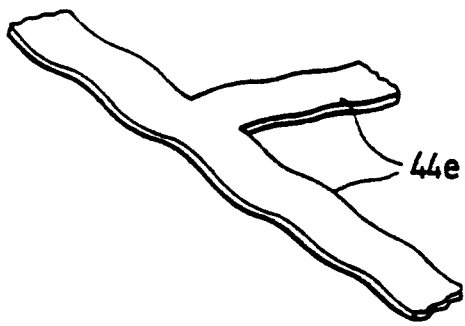
FIG. 5 is an enlarged view of cutout designated by V in FIG. 4.
Figure 6:
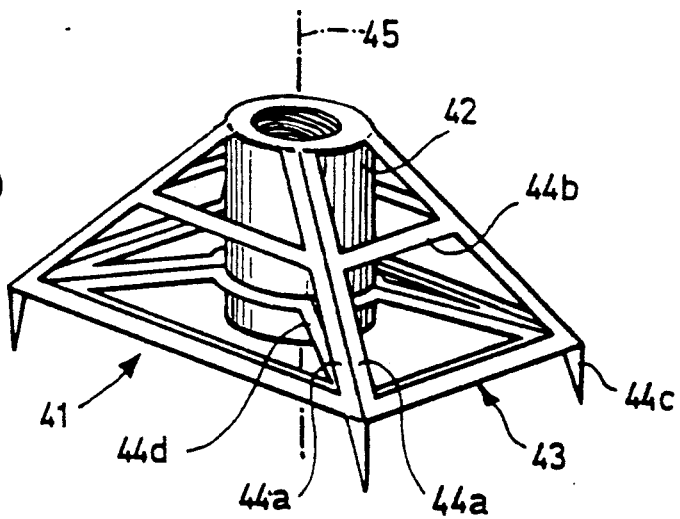
FIG. 6 is a front view of a two-part carrier with a frame as shown in FIG. 4.

Parts of an implant are shown in FIGS. 4, 5 and 6. Carrier 41 has two single piece members and a column-like central portion 42 (see FIG. 6) comprising a threaded bore and a frame 43 surrounding, for all intents and purposes, the central portion 42. The central portion 42 is shaped identically to central portion 2 shown in FIGS. 1-3. The frame 43 is made from the workpiece shown in FIGS. 4 and 5 and has four trapeze-like frame parts 44. The frame parts 44 include longitudinal bars 44a forming two cross-ties each, a transverse bar 44b and spikes 44c for fixing the carrier 41 onto the jawbone. The frame parts 44 further comprise one basic partial element 44d. The longitudinal bars 44a forming the cross-ties, as well as also the transverse bars 44b, are undulated or wave-shaped in such a way that their elevations 44e fulfill the function of the cams or lugs 3d depicted in FIGS. 1-3.

In fabricating the two-part carrier 41 shown in FIG. 6, the workpiece manufactured by punching out of the metal plate is formed into a frame 43. The frame has two longitudinal bars 44a adjoining each other and transverse bar 44b. The frame 43 is then fastened on the end of the central portion 42 along axis 45, by, for instance, being threaded or welded on. The base part elements 44d are thereupon bent towards he central part 42 so that the central part is held in position by the base partial elements 44d. The base partial elements 44d permit the central part 42 to pivot in such a way that its axis assumes a direction deemed necessary by the surgeon and functions independently of the position of the plane defined by the spikes 44c. The treatment of a patient when using the carrier 41 is identical with the treatment methods which have already been described.

The implant and carrier can be modified and varied in many ways. If, for instance, the carrier is manufactured of one of the previously named metals, the carrier may be covered with a thin titanium layer in order to obtain a rough surface which promotes the growing-together and consolidation of the carrier with the newly formed bone tissue.

The shapes and dimensions of the carrier or the implant can also be changed in various ways. The height of the central part of a carrier is preferably between 2 to 8 mm, the length of the base is between 4 to 16 mm and the width of the base approximately 2 to 8 mm.

While the preferred embodiment of the invention has been described in detail, various modifications and adaptations thereof may be made without departing from the spirit and scope of the invention as delineated in the following claims:

We claim:

1. An implant for attaching a substitute tooth or the like onto a jaw or the like, comprising:
    a carrier having a central portion and containing a threaded bore;
    a diaphragm covering said carrier and enabling bone formation;
    a frame surrounding said central portion of the carrier, wherein said frame, further comprises:
    a base formed by transverse ribs;
    longitudinal ribs;
    at least four cross-ties extending from the base edge; and
    at least two spikes on said carrier for fastening the implant into the jawbone.

2. The implant of claim 1, further comprising cams and cross-ties on the carrier, wherein said cams are intended to come to rest upon the jawbone and wherein said diaphragm is fastened onto the side of the central portion.

3. The implant of claim 2, wherein said diaphragm comprises a flexible porous material such as polytetrafluoroethylene.

4. The implant of claim 3, wherein the carrier comprises a single piece casting.

5. The implant of claim 4, further comprising an intermediate piece for fastening the diaphragm to the carrier.

6. The implant of claim 5, further comprising a screw for fastening the diaphragm to the carrier.

* * * * *